United States Patent
Gardner et al.

(10) Patent No.: US 6,210,333 B1
(45) Date of Patent: Apr. 3, 2001

(54) MEDICAL DIAGNOSTIC ULTRASOUND SYSTEM AND METHOD FOR AUTOMATED TRIGGERED INTERVALS

(75) Inventors: Edward A. Gardner; Sriram Krishnan, both of San Jose, CA (US); Nils Sponheim, Oslo (NO)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/416,041

(22) Filed: Oct. 12, 1999

(51) Int. Cl.[7] .................................................. A61B 8/02
(52) U.S. Cl. ................................................... 600/450
(58) Field of Search ......................... 600/440, 437, 600/441, 443, 447, 449, 450, 458; 606/194

(56) References Cited

U.S. PATENT DOCUMENTS

| | | |
|---|---|---|
| 5,024,668 * | 6/1991 | Peters et al. ................... 606/194 |
| 5,456,257 | 10/1995 | Johnson et al. . |
| 5,549,111 | 8/1996 | Wright et al. . |
| 5,551,433 | 9/1996 | Wright et al. . |
| 5,555,534 | 9/1996 | Maslak et al. . |
| 5,570,691 | 11/1996 | Wright et al. . |
| 5,581,517 | 12/1996 | Gee et al. . |
| 5,617,862 | 4/1997 | Cole et al. . |
| 5,675,554 | 10/1997 | Cole et al. . |
| 5,685,308 | 11/1997 | Wright et al. . |
| 5,685,310 | 11/1997 | Porter . |
| 5,694,937 | 12/1997 | Kamiyama . |
| 5,735,281 | 4/1998 | Rafter et al. . |
| 5,833,613 | 11/1998 | Averkiou et al. . |
| 5,846,202 * | 12/1998 | Ramamurthy et al. ............. 600/450 |
| 5,957,845 | 9/1999 | Holley et al. . |

FOREIGN PATENT DOCUMENTS

| | | |
|---|---|---|
| 9901270 | 1/1999 | (GB) . |
| WO 98/32378 | 7/1998 | (WO) . |
| WO 99/35967 | 7/1999 | (WO) . |

OTHER PUBLICATIONS

Kevin Wei, MD., *Quantification of Myocardial Blood Flow With Ultrasound–Induced Destruction of Microbubbles Administered as a Constant Venous Infusion*, Sep. 30, 1997, pp. 473–483.

* cited by examiner

Primary Examiner—Marvin M. Lateef
Assistant Examiner—Ali M. Imam
(74) Attorney, Agent, or Firm—Craig A. Summerfield, Esq.; Brinks Hofer Gilson & Lione

(57) ABSTRACT

A region of interest in the body is imaged using at least two different trigger intervals between images. Imaging automatically switches from one trigger interval to another in response to a user command, such as depressing a button. This automation avoids cumbersome manual changes of the trigger intervals. Perfusion is measured in a shorter time in this way, reducing the effects of breathing and transducer movement. Variation of the trigger intervals allows for a convenient determination of perfusion. For example, the trigger intervals are varied from one heart cycle to two heart cycles and then to other integer numbers of heart cycles.

60 Claims, 2 Drawing Sheets

MEDICAL DIAGNOSTIC ULTRASOUND SYSTEM AND METHOD FOR AUTOMATED TRIGGERED INTERVALS

BACKGROUND

This invention relates to a medical diagnostic ultrasound system and method for automated triggering, such as for use in perfusion imaging or studies. In particular, automated triggering is used for determining perfusion using contrast agents.

Various methods of imaging contrast agents have been proposed for measuring perfusion or perfusion-related parameters. For example, a method is described by Dr. Wei in "Quantification of Myocardial Blood Flow with Ultrasound-Induced Destruction of Microbubbles Administered as a Constant Venous Infusion", Circulation, volume 97, pp. 473–487, 1998. Using an ECG signal, images of microbubbles are generated by an ultrasound system at fixed trigger intervals. As each image is generated after a trigger interval, the microbubbles are destroyed. The amount of contrast agent that reflows into a region of interest during the trigger interval as represented on the subsequent image is measured. A fixed trigger interval is then manually changed and the measurement is repeated. Based on these measurements, a re-flow curve showing the amount of contrast agent flowing into a region as a function of the trigger interval is plotted. Due to the manual change of the trigger interval, an unnecessarily long amount of time is required to acquire the images and measure the amount of contrast agent re-flow.

Other triggering schemes for imaging contrast agents are known, such as shown in U.S. Pat. No. 5,833,613. An ultrasonic transmission is triggered off of an ECG signal to destroy contrast agent. Within the same heartbeat, an image is generated at a certain time after transmission of the destructive ultrasonic energy. The time between the transmission for destruction and transmissions for imaging is varied within the heartbeat. Other triggering schemes are shown for example in U.S. Pat. No. 5,686,310.

To assist a clinician during trigger imaging of contrast agent, images generated using low-power transmission may be interleaved with the trigger or destructive transmissions. The images allow the user to maintain the transducer in the correct position relative to the region of interest with reduced destruction of the contrast agents. Such imaging is taught, for example, in U.S. Pat. No. 6,110,120 (U.S. application Ser. No. 08/838,919), filed Apr. 11, 1997.

BRIEF SUMMARY

The present invention is defined by the following claims, and nothing in this section should be taken as a limitation on those claims. By way of introduction, the preferred embodiments described below include a method and system for triggering to determine perfusion in a body. A region of interest in the body is imaged using at least two different trigger intervals between images. Imaging automatically switches from one trigger interval to another in response to a user command, such as depressing a button. This automation avoids cumbersome manual changes of the trigger intervals. Perfusion is measured in a shorter time in this way, reducing the effects of breathing and transducer movement.

Variation of the trigger intervals allows for a convenient determination of perfusion. For example, the trigger intervals are varied from one heart cycle to two heart cycles and then to other integer numbers of heart cycles.

In one aspect, a medical diagnostic ultrasound system for triggering to determine perfusion in a body is provided. A triggering device, responsive to a periodic signal source, is operable to provide trigger signals. A transmitter transmits pulses in response to the trigger signals. A user interface is operable to receive triggering input, where the triggering device automatically switches from a first predetermined interval between trigger signals to a second, different predetermined interval in response to the triggering input. A method corresponding to the system described above is also provided.

In a second aspect, a medical diagnostic ultrasound system for transmitting pulses to determine perfusion in a body during an imaging session is provided. A triggering device, responsive to an ECG signal source, is operable to provide triggering signals. A transmitter transmits pulses in response to the trigger signals. During the imaging session, the triggering device automatically switches from a first predetermined integer heart cycle interval between trigger signals to a second predetermined integer heart cycle interval, where one of the first and second predetermined integer heart cycle intervals is a greater number of heart cycles than the other.

Further aspects and advantages of the invention are discussed below in conjunction with the preferred embodiments.

DETAILED DESCRIPTION OF THE PREFERRED EMBODIMENTS

Imaging with different trigger intervals allows determination of perfusion. An ultrasound system automatically acquires images separated by these different trigger intervals. For example, two images separated by one-heartbeat intervals are acquired, followed by two images separated by two heartbeat intervals. Switching between the trigger intervals is performed automatically. For example, the system is programmed to switch between intervals after a certain number of images are acquired or automatically switches in response to user input of triggering control information, such as the depression of a button. The user then reviews the acquired images, and/or the system calculates a perfusion parameter from the acquired information.

Automatic switching allows for different trigger intervals during one imaging session without suspending imaging to manually change the trigger interval. Thus, simple and quick determination of a perfusion parameter is provided. The perfusion parameter may be more accurate due to the use of multiple integer heart cycles for the triggering intervals. Depending on the trigger intervals used, a patient may hold their breath while all of the information for determining the perfusion parameter is acquired, minimizing relative transducer and region of interest movement. Furthermore, such techniques allow for repeatability and easier quantification determination by an ultrasound system or other quantification software.

Figure 1:
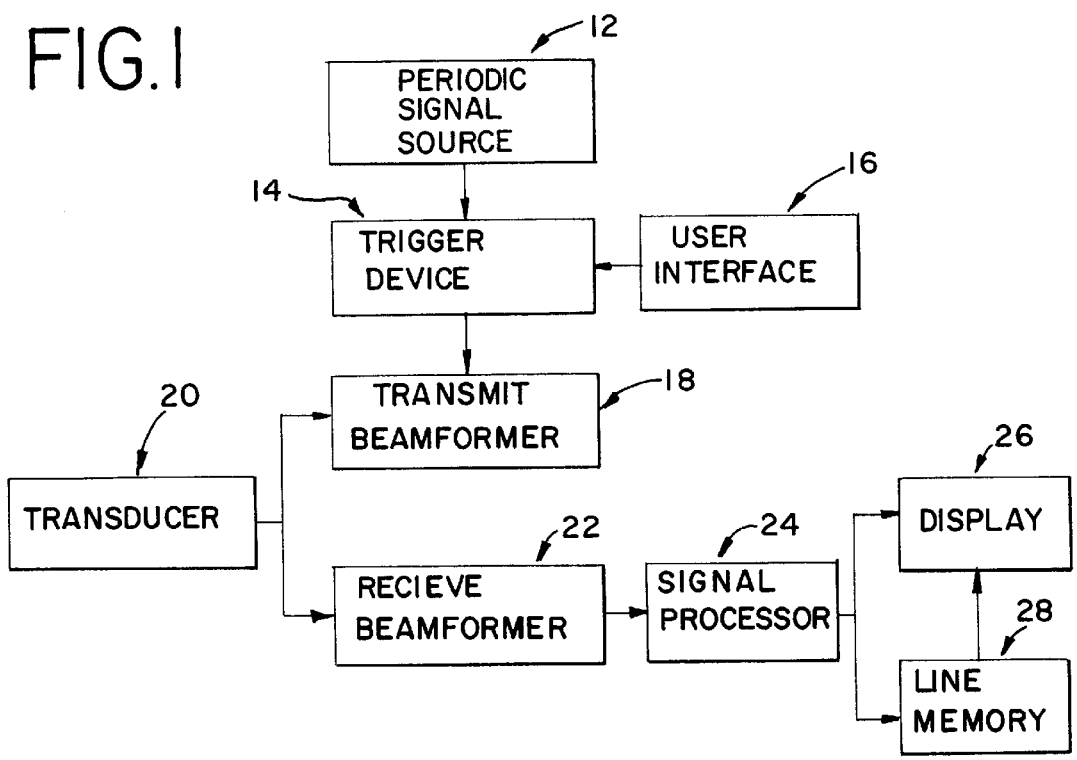
FIG. 1 is a block diagram of one preferred embodiment of a medical diagnostic ultrasound system for triggering to determine perfusion in a body.

Turning now to the drawings, FIG. 1 is a block diagram of one preferred embodiment of a medical diagnostic ultrasound imaging system 10 that incorporates a presently preferred embodiment of this invention. The system 10 includes a periodic signal source generator 12, a trigger device 14, a user interface 16, a transmit beamformer 18, a transducer 20, a receive beamformer 22, a signal processor 24, a display 26, and CINE memory 28. Additional or fewer components may be used in the system 10. For example, the system 10 may not include the CINE memory 28. Both analog and digital systems are suitable. Ultrasound systems marketed by Acuson Corporation under the trade names 128 XP, Aspen and Sequoia are capable of being modified to implement this invention. The Sequoia ultrasound imaging system is described for example in the following patents, assigned to the assignee of the present invention: U.S. Pat. Nos. 5,549,111, 5,551,433, 5,555,534, 5,570,691, 5,581,517, and 5,617,862, the disclosures of which are herein incorporated by reference. Ultrasound systems manufactured by others may also be adapted to implement this invention.

The periodic signal source generator 12 comprises hardware and/or software for generating a periodic signal, such as an ECG device which recognizes the R wave or other portions of an ECG signal, a system clock or timer, a device for monitoring the breathing cycle, or other devices for monitoring periodic functions. In alternative embodiments, the periodic signals source generator 12 includes hardware and/or software for monitoring a combination of signals, such as monitoring the heart cycle relative to the respiration cycle. Periodic signal source generator 12 outputs a signal representing a portion of a period, or a signal representing the variance of a parameter throughout the period.

The trigger device 14 responds to the output of the periodic signal source generator 12 and optionally responds to the user interface 16. The trigger device 14 comprises a processor, a digital signal processor, an ASIC, dedicated hardware or other devices for monitoring the output of the periodic signal source and responsibly generating trigger signals. In one preferred embodiment, the trigger device 14 comprises a transmit beamformer controller, such as disclosed in U.S. Pat. Nos. 5,581,517 and 5,675,554. As another example, the trigger device 14 comprises a controller of the system 10, such as a general processor operating pursuant to software control.

The trigger signals generated by the trigger device 14 comprise a control instruction, a change in a signal, a pulse, or an another signal indicating the beginning of a sequence to transmit and receive acoustic energy. The trigger signals are separated by intervals. Preferably, the intervals are predetermined. As used herein, predetermined is intended broadly to include intervals determined as a function of other inputs during imaging, intervals programmed before imaging, and other intervals that are not just a function of slight physiological changes, such as the natural variance of the heart cycle.

The trigger device 14 is operable to generate trigger signals separated by at least two different intervals. Preferably, at least three different trigger intervals are provided, such as a 1-cycle interval, a 2-cycle interval, a 4-cycle interval, and an 8-cycle interval. Other schemes where at least two different intervals are provided may be used. In one preferred embodiment, the difference between the two intervals is an integer function of the heart cycle, such as one interval being one heart cycle and a second interval being two heart cycles. Alternatively, the intervals are related as a function of a fraction of a periodic cycle. In one preferred embodiment, the different intervals are timed to cause a positive increment between trigger signals (e.g. shortest to longest).

Each trigger signal is used to initiate acquisition of one or more images. For example, two or more trigger signals separated by an interval representing one heart cycle are consecutively generated, resulting in sequential acquisition of two or more respective images separated by one heart cycle each. The trigger device 14 then automatically switches to generating trigger signals separated by a different interval, such as two heart cycles. Any of various triggering schemes, such as generating a different number of trigger signals separated by each of the at least two different (e.g. three trigger signals separated by one heart cycle, followed by two trigger signals separated by two heart cycles). One interval may be used a single or multiple times, such as separating trigger signals at the beginning of a sequence by one heart cycle and at the end of a sequence by one heart cycle.

The trigger device 14 is also responsive to the user interface 16. As used herein, responsive to is intended broadly to include any situation where a first element alters its operation in response to a signal generated by a second element, whether directly or indirectly. Thus, the first element is said to be responsive to the second when the first element responds directly to an output signal of the second element. Similarly, the first element is responsive to the second when intermediate elements or processors alter or modify a signal of the second element before it is applied as an input to the first element.

The user interface 16 comprises a keyboard, a mouse, soft screen key display, and associated hardware and software, a track ball, dedicated buttons, a voice activation system or other devices for receiving input from the user. In one preferred embodiment, the trigger device 14 is programmed in response to input from the user interface 16. For example, various aspects of the triggering scheme are programmed by the user, including one or more of the different intervals, one or more portions of the periodic signal to count or otherwise use for initiating the trigger signals, the order in which the different intervals are used, and the number of triggering signals separated by each interval, and other aspects of the triggering scheme. The user programs these various aspects by selecting a parameter for each individual aspect or by selecting from two or more triggering schemes that include all the aspects of the scheme. In alternative embodiments, the system 10 is pre-programmed through software programming or hardware devices to implement one particular scheme, and the user merely selects triggered imaging for perfusion studies.

During an imaging session, the user interface 16 generates trigger control signals in one embodiment. The trigger control signals indicate a change in the triggering scheme, such as changing from one interval to a second interval between trigger signals. In response, the trigger device 14 automatically switches from generating trigger signals separated by a first interval to trigger signals separated by a second interval. By depressing a button or other device on user interface 16, the user indicates the desire to change the predetermined intervals.

In alternative embodiments, the triggering device 14 automatically switches from one interval to another interval without the triggering control input from the user interface 16. In yet other embodiments, the triggering device 14 is programmed to automatically switch between intervals without input from the user interface 16, but may still receive triggering control input from the user interface 16 to override that programming, or triggering control input is used for automatically switching between one subset of intervals and pre-programming of the triggering device 14 is used for switching in a second different subset of intervals. Regardless of the mechanism for automatically switching between intervals, the triggering device 14 automatically switches between predetermined intervals without manual selection of the interval during the imaging session. As used herein, imaging session comprises the transmission and reception of acoustic energy for imaging without manual alteration of imaging parameters, including predetermined intervals between images. The user does not have to stop acquisition of images in order to change the interval between trigger signals.

In response to the trigger signals, the transmit beamformer 18 generates transmit waveforms for imaging. The transmit beamformer 18 comprises a signal generator, a pulse generator, a pulse shaper, a filter, or other dedicated hardware for generating transmit waveforms. In one preferred embodiment, the transmit beamformer 18 comprises the transmit beamformer disclosed in U.S. Pat. No. 5,675,554, the disclosure of which is herein incorporated by reference. Other transmit beamformers such as transmitters on commercially available ultrasound systems may be used. The transmit beamformer 18 includes digital components, analog components, or combination thereof.

The transmit beamformer 18 generates transmit waveforms centered at a fundamental frequency. The spectral shape, bandwidth and/or transmit power, as well as other characteristics of the transmit waveform, are controlled by the transmit beamformer 18. For example, for reception of signals at harmonics of the fundamental frequency, the transmit waveforms are generated to minimize or eliminate energy at or near the harmonic of the fundamental frequency. In this embodiment, the energy level at the harmonic of the fundamental frequency for each transmit waveform is preferably at least 6 dB, more preferably at least 12 or 20 dB, and most preferably at least 30 dB below the energy level of the fundamental frequency. As another example, a narrow bandwidth is selected for destruction of contrast agents. Likewise, higher powers are used for greater destruction of contrast agents, and conversely, lower power is used to reduce destruction of contrast agents. For example, a low power transmit wave is generated for imaging between triggered images that destroy contrast agent. As another example, high power, narrow bandwidth transmit waveforms are generated to destroy contrast agents without responsive generation of an image. See for example, U.S. application Ser. No. 09/348246, filed Jul. 2, 1999 for Contrast Agent Imaging With Destruction Pulses in Diagnostic Medical Ultrasound, the disclosure of which is herein incorporated by reference. Transmit beamformers 18 capable of controlling none, fewer or additional characteristics of the transmit waveform may be used.

The transmit beamformer 18 immediately begins generation of the transmit waveform in response to the trigger signal. In alternative embodiments, the transmit beamformer 18 begins a count down or otherwise implements a delay from reception of the trigger signal to output of the transmit waveform.

The transmit waveforms are provided to the transducer 20. The transducer 20 generates acoustic energy in response to the transmit waveforms. The transducer 20 also converts reflected ultrasonic energy into electrical signals. The electrical signals are provided to the receive beamformer 22.

The receive beamformer 22 comprises buffers, summers, filters, ASICs, digital signal processors, processors, and other devices for delaying and summing the various signals from the transducer 20. In one preferred embodiment, the receive beamformer 22 comprises the beamformer disclosed in U.S. Pat. No. 5,555,534. The receive beamformers 22 used on commercial systems may be used. The receive beamformer 22 generates data representing a line through a region of interest, such as in phase and quadrature (I/Q) or RF data.

In one embodiment, the receive beamformer 22 includes filters for selectively filtering out one of the fundamental transmit frequency or harmonics of the fundamental transmit frequency. For harmonic imaging, the filter removes or minimizes energies associated with the fundamental frequency bandwidth. Preferably, signals associated with a harmonic frequency, such as the second harmonic, are used for further processing. In another embodiment, energy at fundamental frequencies is used for further processing, regardless of any filtering.

The signals output by the receive beamformer 22 are provided to the signal processor 24. The signal processor 24 comprises one or more digital signal processors, general processors, ASICs, or other dedicated hardware for detecting information from the received signals. For example, a Doppler processor and/or B-mode processor as well as optional spatial and temporal filters are provided for detecting and filtering the data. The signal processor 24 generates acoustic data by detection in any of these various modes. As used herein, acoustic data may also include data output by the receive beamformer or data at various stages of processing prior to and after detection, such as data prior to scan conversion or image data after scan conversion (e.g., ultrasound images).

In one preferred embodiment, the signal processor 24 includes one or more processors, buffers, adders, multipliers, or other dedicated hardware for comparing acoustic data for different images. For example, B-mode intensities or Doppler energies above a threshold level are summed or averaged for each image. Based on a change in the sum or average as a function of the interval between trigger signals, a parameter representing perfusion is calculated. Comparison is also provided by plotting the sums or averages as a function of the trigger interval or the display 26. Other functions and data used for determining the quantities may be used to generate indicia of perfusion, such as calculations disclosed by Wei as discussed above.

Another means for comparing acoustic data to indicate perfusion is the display 26. The display 26 comprises a monitor, LCD or other imaging device and a scan converter or other processors for generating an image from the acoustic data. For comparison, each image associated with a trigger signal is displayed sequentially. Subjectively, an amount of perfusion of the contrast agent into tissue structures is indicated in each image. Differences between the images acquired in response to different trigger intervals also indicate perfusion characteristics.

In alternative embodiments, two or more images acquired at different times are displayed simultaneously. The user subjectively determines an amount of perfusion or other perfusion characteristic by comparing the two images, such as an image associated with a single heart cycle interval as compared to an image associated with a two heart cycle interval. In one embodiment, all the images associated with a same triggering interval are averaged and displayed adjacent to an average of images associated with different intervals. Other imaging schemes, including sequential or simultaneous display of B-mode, M-mode, Doppler or other display modes or combinations thereof may be used.

Simultaneous display for comparison is preferred to assess myocardial perfusion, since echo cardiographers are better able to distinguish artifacts from perfusion when presented with side-by-side images. Any quantities and associated graphs are preferably displayed during the imaging session in real time, but may be displayed after the imaging session.

The acoustic data is also stored in the CINE memory 28. The CINE memory 28 comprises a buffer, RAM, or other memory device operable to re-generate the acquired images, such as for later sequential or simultaneous generation of images. Alternatively or additionally, a tape, diskette or other moveable memory device is provided to store acoustic data or generated images for later imaging or quantification.

Figure 2:
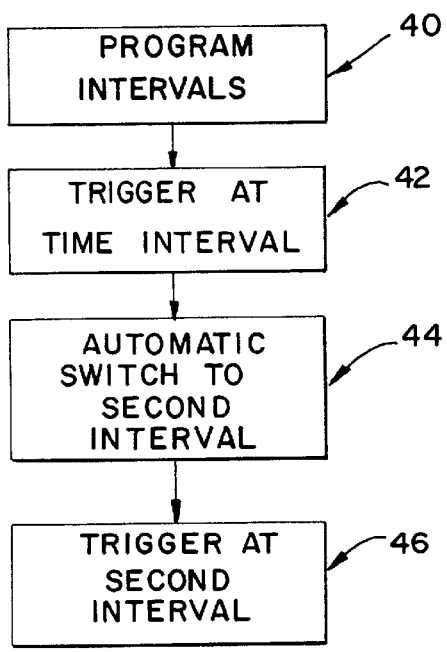
FIG. 2 is flow chart representing one preferred embodiment of the operation of the system of FIG. 1.

Referring to FIG. 2, one embodiment of a process for triggering to determine perfusion in a body is shown. In act 40, at least two different trigger intervals are programmed into the system 10. The user selects a number of periods for each interval and/or a delay for each interval. For example, the user selects one or more ECG R waves and a delay sufficient to place the trigger signal at the systole portion of the heart cycle. The selection is made for each interval, such as selecting a different integer number of heart cycles for each interval and a same or a different delay. In alternative embodiments, only a delay or only a number of cycles are selected. The user also selects the number of acquisitions or images to be acquired using any given interval. In alternative embodiments, the system 10 selects the various intervals and associated parameter using pre-programmed information, such as based on a selected imaging application. In yet other alternative embodiments, the user selects from two or more pre-programmed triggering sequences.

In act 42, imaging is triggered at a first interval. For example, based on an initiation signal (e.g. triggering input) from the user interface 16 or a pre-programmed delay after a particular image, a counter counts cycles or an amount of time before acquiring a first image. Preferably, the amount of time or number of cycles is the same as or longer than the first interval. A selected number of images are then acquired separated by the first interval. Where the interval is an integer number of cycles, the triggering signals are provided for each of those integer number of cycles. Preferably, each image or associated acoustic data is stored after initiation of the triggering sequence. For example a video or frame buffer, CINE memory or a DIMAQ format image is stored.

In act 44, generating trigger signals at the first interval automatically switches to generating trigger signals at the second interval. As discussed above, the automatic switching occurs in response to triggering control signals from the user interface 16 or pre-programming of the system 10. For example, the system 10 automatically switches from one interval to another interval after acquiring a pre-determined or selected number of images or in response to depression of a button.

In act 46, acquisition of images and the associated transmissions are triggered at a second interval. In one embodiment, the first and second intervals are both integer number of heart cycles, such as a first interval of one heart cycle and a second interval of two heart cycles. An amount or other characteristic is determined as a function of the acoustic data or images acquired at the two different trigger signal intervals.

Figure 3:
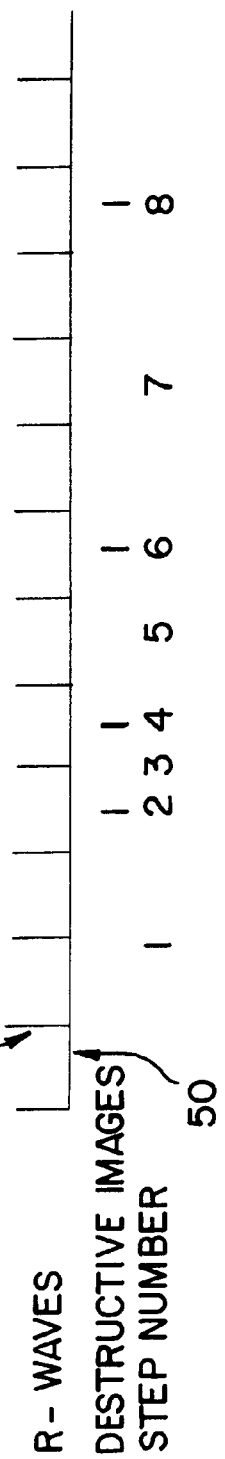
FIG. 3 is a graphical representation of one preferred embodiment of a triggering scheme.

Referring to FIGS. 1 and 3, one embodiment of a preferred triggering scheme is shown. A pulse train 50 representing periodic signals indicative of the R wave portion of a heart cycle are provided by the periodic signal source 12. The pulse train 50 includes a pulse 52 at each R wave.

Below the pulse train 50 in FIG. 3 are act numbers 1 through 8 indicating various acts that occur as part of the triggering scheme. In act 1, imaging is ceased for 10 or more heart cycles. Preferably, all ultrasonic transmission cease, but low power or other energy that does not destroy or minimally affects perfusion of contrast agents may occur. After 10 or more heartbeats, ultrasonic energy is transmitted for generating an image in act 2. Preferably, the ultrasonic transmissions are associated with a high power to destroy contrast agents throughout the region of interest being imaged. The transmission and associated image are synchronized to occur at a specific time after the R wave pulse 52. The specific time is preferably chosen to coincide within systole. Preferably, all triggered transmissions and associated images are generated at the same portion of the heartbeat. In act 3, the triggering device 14 generates the next trigger signal after one heart cycle. In act 4, transmissions and associated images are generated. The same or different transmit waveforms may be used as are used for transmission in act 2. The resulting image demonstrates the amount of perfusion of contrast agent after one heartbeat in the region of interest. The trigger device 14 automatically switches to a two heart cycle interval and waits for two heart cycles in act 5. In act 6, transmissions and associated images are generated, demonstrating perfusion after two heart cycles. The trigger device 14 automatically switches to a four heart cycle interval in act 7. After waiting four heart cycles, transmissions and associated images are generated in act 8. The resulting image shows the amount of perfusion after four heart cycles. Preferably, all of the transmissions associated with this embodiment are high-power transmissions with a high density of scan lines to destructively image contrast agents.

Figure 4:
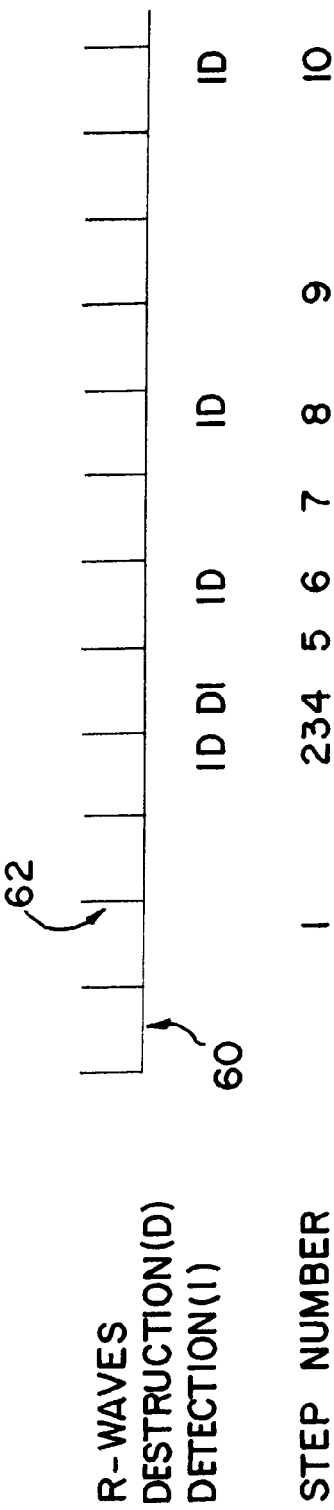
FIG. 4 is a graphical representation of another preferred embodiment of a triggering scheme.

Referring to FIG. 4, another preferred embodiment of a triggering scheme is shown and includes transmissions for destroying contrast agents without generating corresponding images. A pulse train 60 including pulses 62 representing the occurrence of an R wave is shown. In act 1, imaging and associated transmissions are ceased for 10 or more heart cycles (e.g. 10 or more pulses 62). In act 2, ultrasonic energy is transmitted and reflections received to detect and image contrast agents. The transmissions for imaging may be low power or high power. The transmission is synchronized to occur at a specific time after the R wave, preferably chosen to coincide within systole. Other delays or no delay after the pulse 62 may be selected. Immediately after transmission and reception for imaging, ultrasonic energy is transmitted to destroy any remaining contrast agents. Preferably, the destructive transmissions are high power, narrow bandwidth signals. In act 3, transmissions or at least transmissions substantially destructive of contrast agents are ceased for an interval of one heart cycle. In act 4, the transmissions of act 2 are repeated in reverse order. The transmission of the destructive beam precedes the transmission of the beam for imaging. The resulting image represents tissue and substantially no contrast agent. In act 5, the triggering device 14 provides trigger signals still separated by one heart cycle. In act 6, transmissions associated with imaging are generated and then followed by transmissions associated with destruction of contrast agents. The resulting image shows the amount of perfusion or re-flow of contrast agent after one heart cycle. In act 7, the triggering device 14 automatically switches to a two heart cycle interval. In act 8, transmissions for imaging are followed by transmissions for destruction. The resulting image represents perfusion or re-flow of contrast agent after two heart beats. In act 9, the triggering device 14 automatically switches to providing triggering signals separated by an interval of four heart cycles. In act 10, transmissions associated with first imaging and secondly with destruction of contrast agents are generated. The resulting image represents the amount of reflow or perfusion by contrast agents after four heart cycles.

The images acquired using the schemes of either of FIGS. 3 or 4 are preferably simultaneously displayed. In alternative embodiments, more than one transmissions and associated multiple images responsive to any single interval may be acquired. In other embodiments, the partial cycle delays associated with each interval vary as a function of the interval. Thus, depending on the interval, an image representing a different portion of the heart cycle is created. In yet other alternative embodiments, a sequence of images responsive to the same integer number of heart cycles separation but with a swept delay to image different portions of the heart cycle is used, followed by swept delay after a different number of integer heart cycles.

Triggered or non-triggered additional low power transmissions for imaging without or with minimal destruction of contrast agents may be provided. Preferably, these transmissions are generated to minimize destruction of contrast agent, such as disclosed in U.S. Pat. No. 6,110,120 (Ser. No. 08/838,919) filed Apr. 11, 1997, the disclosure of which is herein incorporated by reference. These low power transmissions can be used to maintain image orientation or location during a perfusion assessment imaging session. In one embodiment, the system performs low-power, fundamental imaging whenever the system is not producing triggered images (i.e., locator imaging between triggered images). These orientation or location images preferably occur with sufficient frequency to produce real time images and are suspended when a triggered image is acquired. The operator may react to patient motion in order to maintain a constant image plane position and thus improve the accuracy of comparisons between the triggered images. Preferably, these low power transmissions are timed to occur at specific points during the triggering interval. In one embodiment, the low power transmissions are suspended for a period after each high-power transmission associated with triggering. In alternative embodiments, the system 10 does not generate any additional transmissions other than those associated with the triggering signals.

While the invention has been described above by reference to various embodiments, it is to be understood that many changes and modifications can be made without departing from the scope of the invention. For example, various triggering schemes may be developed through testing and as a function of different imaging applications. The techniques described herein may be used for such triggering schemes.

It is therefore intended that the foregoing detailed description be understood as an illustration of the presently preferred embodiments, and not as a definition of the invention. It is only the following claims, including all equivalents, that are intended to define the scope of this invention.

What is claimed is:

1. A medical diagnostic ultrasound system for triggering to determine perfusion in a body, the system comprises:
    a periodic signal source generator;
    a triggering device responsive to the periodic signal source generator and being operable to provide trigger signals;
    a transmitter for transmitting pulses in response to the trigger signals; and
    a user interface operable to receive triggering input and operable to receive input for pre-programming first and second pre-determined intervals, the second pre-determined interval different than the first pre-determined interval;
    wherein the triggering device automatically switches from the first pre-determined interval between trigger signals to the second pre-determined interval in response to the triggering input.

2. The system of claim 1 wherein the periodic signal source generator is an ECG signal generator.

3. The system of claim 2 wherein the first and second pre-determined intervals are respective functions of integer numbers of heart cycles.

4. The system of claim 3 wherein the first and second pre-determined intervals vary by increasing the number of heart cycles between the trigger signals.

5. The system of claim 4 comprising at least a third pre-determined interval different than the first and second pre-determined intervals.

6. The system of claim 5 wherein the triggering device is operable to provide trigger signals separated by the first pre-determined interval during a first sequence, automatically switch to provide trigger signals separated by the second pre-determined interval during a second sequence, and automatically switch to provide trigger signals separated by the third pre-determined interval during a third sequence, wherein the first, second and third sequences comprise a single imaging session.

7. The system of claim 6 wherein the triggering device switches between the first, second and third sequences in response to user input.

8. The system of claim 5 wherein the first, second and third predetermined intervals comprise one, two and four heart cycles, respectively.

9. The system of claim 1 wherein the periodic signal source generator is a system clock or timer.

10. The system of claim 1 wherein at least two of the first and second pre-determined intervals vary by a positive increment.

11. The system of claim 1 wherein the transmitter is operable to transmit pulses for location imaging in addition to the pulses responsive to the trigger signals.

12. The system of claim 11 wherein the triggering input comprises a signal generated in response to depression of a button.

13. The system of claim 1 further comprising a processor operable to estimate perfusion.

14. The system of claim 1 further comprising a receive beamformer for receiving echo signals in response to the transmitted pulses.

15. The system of claim 14 further comprising means for storing acoustic data responsive to the echo signals.

16. The system of claim 15 further comprising means for comparing stored acoustic data obtained in response to different pre-determined triggering intervals.

17. The system of claim 16 further comprising a display of comparison results.

18. The system of claim 15 further comprising a simultaneous display of at least first and second images based on scan converted stored acoustic data and each responsive to a different one of the first and second pre-determined intervals.

19. A method for triggering transmission to determine perfusion in a body during an imaging session with a medical diagnostic ultrasound system, the method comprising the acts of:
    (a) providing a periodic signal;
    (b) generating trigger signals responsive to the periodic signal;

(c) transmitting acoustic pulses in response to the trigger signals;

(d) inputting triggering control information from a user interface during the imaging session;

(e) automatically switching from a first pre-determined interval between trigger signals to a second different, pre-determined interval in response to the triggering control information; and (f) pre-programming the first and second intervals in response to user input.

20. The method of claim 19 wherein act (a) comprises inputting an ECG signal.

21. The method of claim 20 wherein the first and second pre-determined intervals are respective functions of integer numbers of heart cycles.

22. The method of claim 21 wherein the second pre-determined intervals differs from the first pre-determined interval by an increase in the number of heart cycles between the trigger signals.

23. The method of claim 19 wherein act (a) comprises providing a system clock or timer.

24. The method of claim 19 wherein the first and second pre-determined intervals vary by a positive increment.

25. The method of claim 19 further comprising:

(g) automatically switching from the second pre-determined interval to a third pre-determined interval different than the first and second pre-determined intervals.

26. The method of claim 25 wherein act (b) comprises generating trigger signals separated by the first pre-determined interval during a first sequence, separated by the second pre-determined interval during a second sequence, and separated by the third pre-determined interval during a third sequence, wherein the first, second and third sequences comprise a single imaging session.

27. The method of claim 26 wherein act (e) comprises automatically switching between the second and third sequences in response to user control information.

28. The method of claim 25 wherein the first, second and third predetermined intervals comprise one, two and four heart cycles, respectively.

29. The method of claim 19 further comprising:

(g) transmitting pulses for location imaging in addition to (c).

30. The method of claim 19 further comprising:

(g) estimating a perfusion parameter.

31. The method of claim 19 wherein act (d) comprises depressing a button.

32. The method of claim 19 further comprising:

(g) storing acoustic data responsive to the transmitted pulses; and (h) comparing stored acoustic data obtained in response to different pre-determined triggering intervals.

33. The method of claim 32 further comprising a display of comparison results.

34. The method of claim 32 wherein act (h) comprises simultaneously displaying at least first and second images based on scan converted stored acoustic data and each responsive to a different one of the first and second pre-determined intervals.

35. A medical diagnostic ultrasound system for transmitting pulses to determine perfusion in a body during an imaging session, the system comprising:

an ECG signal source;

a triggering device responsive to the ECG signal source and being operable to provide trigger signals; and a transmitter for transmitting pulses in response to the trigger signals;

wherein, during the imaging session, the triggering device automatically switches from a first pre-determined integer heart cycle interval between trigger signals to a second pre-determined integer heart cycle interval, one of the first and second pre-determined integer heart cycle intervals corresponding to a greater number of heart cycles than the other of the first and second pre-determined integer heart cycle interval.

36. The system of claim 35 further comprising at least a third pre-determined integer heart cycle interval different than the first and second pre-determined intervals.

37. The system of claim 36 wherein the triggering device is operable to provide trigger signals separated by the first pre-determined interval during a first sequence, automatically switch to provide trigger signals separated by the second pre-determined interval during a second sequence, and automatically switch to provide trigger signals separated by the third pre-determined interval during a third sequence, wherein the first, second and third sequences comprise a single imaging session.

38. The system of claim 37 wherein the triggering device switches between the first, second and third sequences in response to user triggering control input.

39. The system of claim 38 wherein the triggering control input comprises a signal generated in response to depression of a button.

40. The system of claim 36 wherein the first, second and third predetermined intervals comprise one, two and four heart cycles, respectively.

41. The system of claim 35 wherein the first and second pre-determined intervals are pre-programmed.

42. The system of claim 41 wherein a user-interface is operable to receive input for pre-programming the first and second pre-determined intervals.

43. The system of claim 35 further comprising:

a receive beamformer for receiving echo signals in response to the transmitted pulses;

a means for storing acoustic data responsive to the echo signals; and a means for comparing stored acoustic data obtained in response to different pre-determined triggering intervals.

44. The system of claim 43 further comprising a display of comparison results.

45. The system of claim 43 further comprising a simultaneous display of at least first and second images based on scan converted stored acoustic data and each responsive to a different one of the first and second pre-determined intervals.

46. The system of claim 35 wherein the transmitter is operable to transmit pulses adapted to minimize destruction of contrast agent between the trigger signals.

47. The system of claim 46 wherein the adaptation comprises transmitting pulses with a lower power than the pulses responsive to the trigger signals.

48. A method for transmitting pulses to determine perfusion in a body during an imaging session with a medical diagnostic ultrasound system, the method comprising the acts of:

(a) providing an ECG signal;

(b) generating trigger signals in responsive to the ECG signal;

(c) transmitting pulses in response to the trigger signals; and (d) during the imaging session, automatically switching from a first pre-determined integer heart cycle interval between trigger signals to a second pre-determined integer heart cycle interval, one of the first and second pre-determined integer heart cycle intervals being a greater number of heart cycles than the other of the first and second pre-determined integer heart cycle interval.

49. The method of claim 48 further comprising:

(e) automatically switching from the second pre-determined interval to a third pre-determined integer heart cycle interval different than the first and second pre-determined intervals.

50. The method of claim 49 wherein act (b) comprises generating trigger signals separated by the first pre-determined interval during a first sequence, separated by the second pre-determined interval during a second sequence, and separated by the third pre-determined interval during a third sequence, wherein the first, second and third sequences comprise a single imaging session.

51. The method of claim 50 wherein act (d) comprises switching between the first, second and third sequences in response to user triggering control input.

52. The method of claim 51 further comprising:

(e) depressing a button, wherein the user triggering control input is response to the depression of the button.

53. The method of claim 48 further comprising:

(e) receiving echo signals in response to the transmitted pulses;

(f) storing acoustic data responsive to the echo signals; and (g) comparing stored acoustic data obtained in response to different pre-determined triggering intervals.

54. The method of claim 53 wherein act (g) comprises displaying the comparison results.

55. The method of claim 53 wherein act (g) comprises simultaneously displaying at least first and second images based on scan converted stored acoustic data and each responsive to a different one of the first and second pre-determined intervals.

56. The method of claim 49 wherein the first, second and third predetermined intervals comprise one, two and four heart cycles, respectively.

57. The method of claim 48 wherein the first and second pre-determined intervals are pre-programmed.

58. The method of claim 57 further comprising:

(e) pre-programming the first and second pre-determined intervals with a user interface.

59. The method of claim 48 further comprising:

(e) transmitting pulses adapted to minimize destruction of contrast agent.

60. The method of claim 59 wherein (e) comprises transmitting pulses with a lower power than the pulses of (c).

* * * * *